United States Patent [19]

Henley

[11] Patent Number: 5,459,409
[45] Date of Patent: Oct. 17, 1995

[54] TESTING DEVICE FOR LIQUID CRYSTAL DISPLAY BASE PLATE

[75] Inventor: Francois J. Henley, Los Gatos, Calif.

[73] Assignee: Photon Dynamics, Inc., Milpitas, Calif.

[21] Appl. No.: 757,458

[22] Filed: Sep. 10, 1991

[51] Int. Cl.⁶ .................... G01R 31/00; G01R 31/302; G02F 1/13
[52] U.S. Cl. .............................. 324/770; 324/530
[58] Field of Search ................... 324/73 R, 770, 324/751–753

[56] References Cited

U.S. PATENT DOCUMENTS

| | | | |
|---|---|---|---|
| 3,780,271 | 12/1973 | Sharkitt et al. | 235/61.11 E |
| 3,786,431 | 1/1974 | Bouchet et al. | 340/172.5 |
| 3,949,363 | 4/1976 | Holm | 340/146.3 D |
| 3,992,663 | 11/1976 | Seddick | 324/52 |
| 4,242,635 | 12/1980 | Burns | 324/158 |
| 4,355,278 | 10/1982 | Burns et al. | 324/158 |
| 4,368,523 | 1/1983 | Kawate | 365/63 |
| 4,444,801 | 4/1984 | Hongo et al. | 427/10 |
| 4,463,073 | 7/1984 | Miyauchi et al. | 430/5 |
| 4,465,969 | 8/1984 | Tada et al. | 324/96 |
| 4,507,605 | 3/1985 | Geisel | 324/73 |
| 4,510,222 | 4/1985 | Okunaka et al. | 430/5 |
| 4,523,847 | 6/1985 | Bjorklund et al. | 356/349 |
| 4,542,333 | 9/1985 | Koontz | 324/52 |
| 4,563,093 | 1/1986 | Tada et al. | 356/368 |
| 4,618,819 | 10/1986 | Mourou et al. | 324/77 |
| 4,631,576 | 12/1986 | St. John | 358/65 |
| 4,633,242 | 12/1986 | Sekiya | 340/719 |
| 4,636,403 | 1/1987 | Fisanick et al. | 427/53 |
| 4,688,900 | 8/1987 | Doane et al. | 350/347 |
| 4,718,064 | 1/1988 | Edwards et al. | 371/20 |
| 4,727,234 | 2/1988 | Oprysko et al. | 219/121 |
| 4,742,521 | 5/1988 | Nishida | 371/54 |
| 4,758,092 | 7/1988 | Heinrich et al. | 356/36 |
| 4,760,330 | 7/1988 | Lias, Jr. | 324/73 R |
| 4,776,022 | 10/1988 | Fox et al. | 382/8 |
| 4,819,038 | 4/1989 | Alt | 357/4 |
| 4,825,201 | 8/1989 | Watanabe et al. | 340/717 |
| 4,855,591 | 8/1989 | Nakamura et al. | 250/225 |
| 4,862,075 | 8/1989 | Choi et al. | 324/158 |
| 4,868,492 | 11/1989 | Beha et al. | 324/73 |

(List continued on next page.)

FOREIGN PATENT DOCUMENTS

| | | |
|---|---|---|
| 3111393A1 | 9/1982 | Germany . |
| 55-56330 | 11/1981 | Japan . |
| 55-58893 | 11/1981 | Japan . |

OTHER PUBLICATIONS

System Tests Devices at GHz Rates, Lyle H. McCarty, Design News, Apr. 10, 1989.

(List continued on next page.)

Primary Examiner—Kenneth A. Wieder
Assistant Examiner—Barry C. Bowser
Attorney, Agent, or Firm—Townsend and Townsend and Crew

[57] ABSTRACT

The present invention provides an electro-optical element arranged to face a liquid crystal base plate, an electric source to impress an electric voltage between them, a source of light for irradiating light on the electro-optical element, a light detector to receive the reflected light from the electro-optical element, and a mounting device for fixing the liquid crystal base plate in a fixed position. The mounting device has a highly flat surface, groove thereon and vacuum attaches the liquid crystal base plate on the surface of the base platform. Light irradiates a reflective layer located on the lower surface of an electro-optical element which is in close proximity to the liquid crystal display base plate. A voltage is applied across the electro-optical element and the light reflected by the electro-optical element are measured. The optical characteristics of the electro-optical element is measured. The optical characteristics of the electro-optical element change in proportion to the electric field across it. The electric field is supplied in part by the liquid crystal display base plate being tested. Thus, by measuring the reflected light, the integrity of the liquid crystal display base plate is evaluated.

19 Claims, 7 Drawing Sheets

U.S. PATENT DOCUMENTS

| | | | |
|---|---|---|---|
| 4,875,006 | 10/1989 | Henley et al. | 324/158 |
| 4,899,105 | 2/1990 | Akiyama | 324/158 |
| 4,906,922 | 6/1990 | Takahashi et al. | 324/158 |
| 4,910,458 | 3/1990 | Forsyth et al. | 324/158 |
| 4,939,353 | 7/1990 | Iijima | 235/438 |
| 4,944,576 | 7/1990 | Lacker et al. | 350/334 |
| 4,983,911 | 1/1991 | Henley | 324/158 |
| 4,999,577 | 3/1991 | Beha et al. | 324/158 |
| 5,017,755 | 5/1991 | Yahagi et al. | 219/121 |
| 5,037,683 | 7/1991 | Takahashi et al. | 324/158 |
| 5,043,297 | 8/1991 | Suzuki et al. | 437/51 |
| 5,122,737 | 6/1994 | Clauberg | 324/158 R |
| 5,140,145 | 8/1992 | Bianco | 235/462 |
| 5,243,602 | 9/1993 | Akagi, Jr. | 371/25.1 |

OTHER PUBLICATIONS

Electro–Optic Device Tester Tops 1 GHz, John Novellino, Electronic Design, Sep. 8, 1988.

An Ultra High Speed Test System, Francois J. Henley, IEEE Design & Test of Computers, Feb. 1989.

Electro–Optic Technology Supports Gigahertz Speeds; Francois J. Henley, Electronics Test, Sep. 1988.

Using Electro–Optic Sampling Technology For Accurate Gigahertz ATE: Overview of the Art, Francois J. Henley, 1990 IEEE VLSI Test Symposium.

High Speed Pattern Generator and GaAs Pin Electronics For a Gigahertz Production Test System, D. J. Kratzer, S. Barton, F. J. Henley D. A. Plomgrem, Proceedings of IEEE 1988 Int'l Test Conf, Sep. 1988.

Test Head Using Electro–Optic Receivers and GaAs Pin Eloectronics for a Gigahertz Production Test System, F. J. Henley, H. J. Choi, Proceedings of IEEE 1988 Int'l Test Conference, Sep. 1988.

Achieving ATE Accuracy at Gigahertz Test Rates: Comparison of Electronic and Electro–Optic Sampling Technologies, F. J. Henley, H. J. Choi, Int'l Test Conf. Aug., 1989.

Systems Solutions Based on Electro–Optic Sampling to High Speed IC Test Problems, F. J. Henley, D. B. MacDonald, SPIE vol. 795 Characterization of Very High Speed Semiconductor Devices & Integrated Circuits (1987) pp. 345–351.

Characterization of High Speed (Above 500 MHz) Devices Using Advanced ATE–Techniques, Results and Device Problems, S. Barton, Proceedings of the IEEE 1989, Int'l Test Conf., Aug. 1989.

Testing and Qualifications of a–Si TFT–LC Color Cells for Military Avionics Applications; F. C. Luo et al.; SID 90 Digest; pp. 194–196, 1990.

Measurement of Electro–Optic Characteristics of LCDs; M. E. Becker et al.; SID 90 Digest; pp. 163–166, 1990.

Testing and Qualificastions of a Si TFT–LC Color Cells for Military Avionics Applications; F. C. Luo et al; SID 90 Digest; pp. 194–196, 1990.

In–Process Testing of Thin Film Transistor Arrays; R. Wisnieff et al.; SID 90 Digest pp. 190–193, 1990.

NCAP Displays: Optical Switching and Dielectric Properties; L. Welsh et al.; SID 90 Digest; pp. 220–223, 1990.

TESTING DEVICE FOR LIQUID CRYSTAL DISPLAY BASE PLATE

BACKGROUND OF THE INVENTION

The present invention relates to a testing device for testing defects in liquid crystal display base plates used for such as liquid crystal display panels.

A method called the Active Matrix Method is in use as a high image data resolution liquid crystal panel used in liquid crystal televisions, and the like. This involves providing a switch circuit to each image element with a thin film transistor. Products have appeared having from 250,000–500,000 to more than 1,000,000 pixels.

To manufacture Active Matrix Method liquid crystal display panels, the technique was to first produce an active matrix liquid crystal display base plate (hereafter called liquid crystal base plate) by arranging pixel elements in matrix form. Facing each image element on the base plate and formed at the same time is gate wiring and source wiring common to each pixel element and thin film transistors corresponding to each pixel element. Opposing transparent base plates are then arranged through spacers on the liquid crystal base plate, and liquid crystal is enclosed in the space formed between the liquid crystal base plate and the transparent base plate.

SUMMARY OF THE INVENTION

Liquid crystal base plates are formed by numerous pixel elements terminals, their corresponding wiring and thin film transistors and are manufactured by various film forming processes in a clean room to minimize dust. However, the presence of even slight micro dusts in the production atmosphere is directly related to breaking defects and short circuiting defects of the pixel elements, gate wiring and source wiring, etc. This is because the size of each pixel element and the width of the wiring in the liquid crystal base plate are extremely small. Up to about 10 of such defects for one liquid crystal base plate can be tolerated. Especially in manufacturing liquid crystal base plate having high pixel data resolution, it is extremely difficult to keep the number of defects below tolerance limits and the defect rate is remarkably high.

In manufacturing liquid crystal base plates, it is necessary to test the quality of the manufactured liquid crystal base plate. In the past there was no effective means to test the quality of the liquid crystal base plate per se in the manufacturing process. For this reason tests were carried out visually for the first time after the liquid crystal display panel had been completed by energizing the liquid crystal base plate to determine whether each pixel element was functioning. However, in such a situation it is difficult to carry out repairs on the liquid crystal base plate even if a flaw is discovered through tests, and nothing can be done but to treat the product as waste. This has become one factor impeding the increase in yield and decrease of production cost of the Active Matrix Method liquid display panel.

The present invention was made in consideration of this situation, and its objective is to provide a device that is able to test for defects in liquid crystal base plates per se, used in liquid crystal display panels.

The present invention is characterized by having an electro-optical element whose optical characteristics change when an electric field is applied across it, arranged in very close proximity to the liquid crystal display base plate. A voltage is then applied across the electro-optical element, with one side of the applied voltage being applied to each pixel element of the liquid crystal display base plate. Light is irradiated from the back side of the electro-optical element and reflected light is received on a detection device and observed. A mounting device is used to hold the liquid crystal base plate during testing. The mounting device has a flat surface and has a base platform arranged so that the liquid crystal display base plate adheres to the surface of the base platform by cutting a groove on the surface of the basic platform and applying a vacuum to the groove, thereby holding the liquid crystal base plate in place.

The electro-optical element's optical characteristics change when the electric field is impressed across it. This electro-optical element is arranged adjacent to the liquid crystal base plate, and a voltage is applied between the pixel element terminal of the liquid crystal base plate and the electro-optical element. The electric field generated by each pixel element changes in accordance with the existence and condition of defects in the liquid crystal base plate. Changes in the optical characteristics of the electro-optical element will result. By irradiating light from the light source on the electro-optical element, receiving the reflected light on a light detector and observing the intensity of the reflected light, the extent of the change in the optical characteristics of the electro-optical element can be detected, and thereby the existence and condition of defects in the liquid crystal base plate can be discovered.

In the test apparatus, the liquid crystal base plate is vacuum attached to the surface of the base platform by applying a vacuum to the groove formed on the surface of the base platform. Consequently, by finishing the surface of the base platform sufficiently flat, even if warping and sinuosity problems exist with the liquid crystal base plate, such warping and sinuosity will not be a factor during testing.

DESCRIPTION OF A PREFERRED EMBODIMENT

Figure 1:
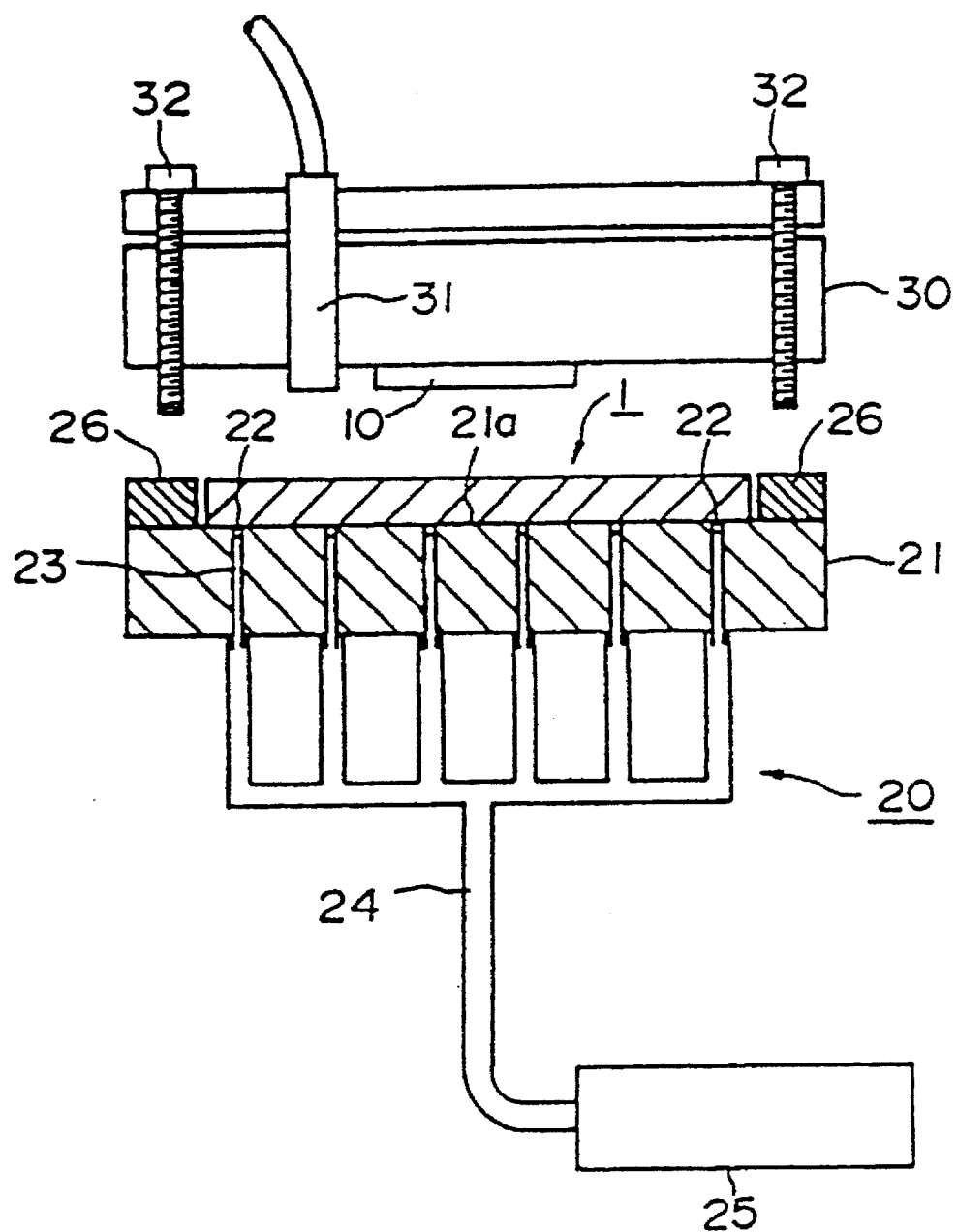
FIG. 1 is an outline of the mounting device in the test apparatus of one implementation of the present invention.

The test apparatus of the present invention will be explained by referring to the drawings.

Figure 7:
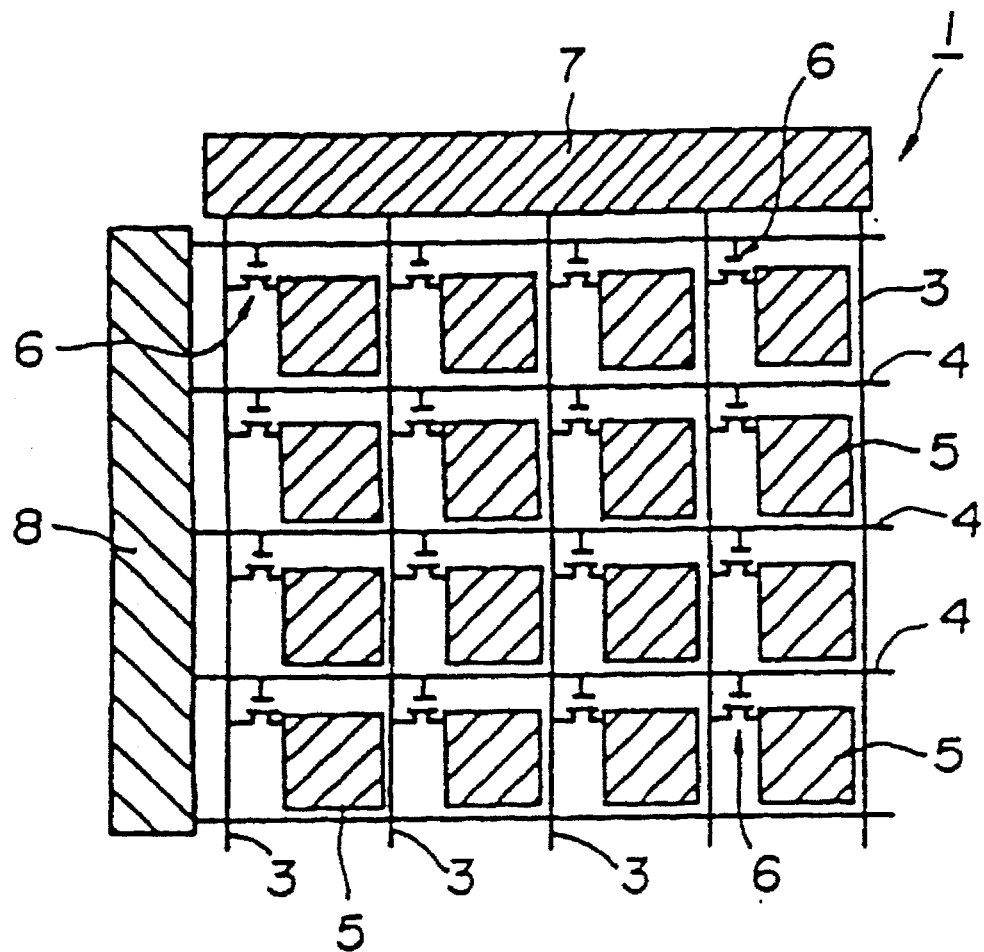
FIG. 7 is a drawing showing an example of a liquid crystal base plate.

First, the liquid crystal base plate shown in FIG. 7 will be explained. This is a diagram of a Liquid Crystal Base Plate 1, which is well known for use in liquid crystal display panels, and the like. Source Wiring 3 for passing data signals and Gate Wiring 4 for passing scanning signals are formed on the surface of Base Plate 2 which is made of glass, or the
} like. A Pixel Element Terminal 5 is formed between Source Wiring 3 and Gate Wiring 4. It is constructed so that Pixel Element 5 is connected with Source Wiring 3 and Gate Wiring 4 through Thin Film Transistor 6 which serves as the switching element. Reference number 7 is a shorting-bar connected to Source Wiring 3, and number 8 is a shorting-bar connected to Gate Wiring 4. These Shorting-Bars 7 and 8 prevent static electricity from damaging Thin Film Transistor 7. They are also used to impress an electric voltage on Pixel Element Terminal 5 through Source Wiring 3 and Gate Wiring 4 at the time of testing as explained below. Shorting-Bars 7 and 8 are severed and removed when Liquid Crystal Base Plate 1 is completed.

Figure 6:
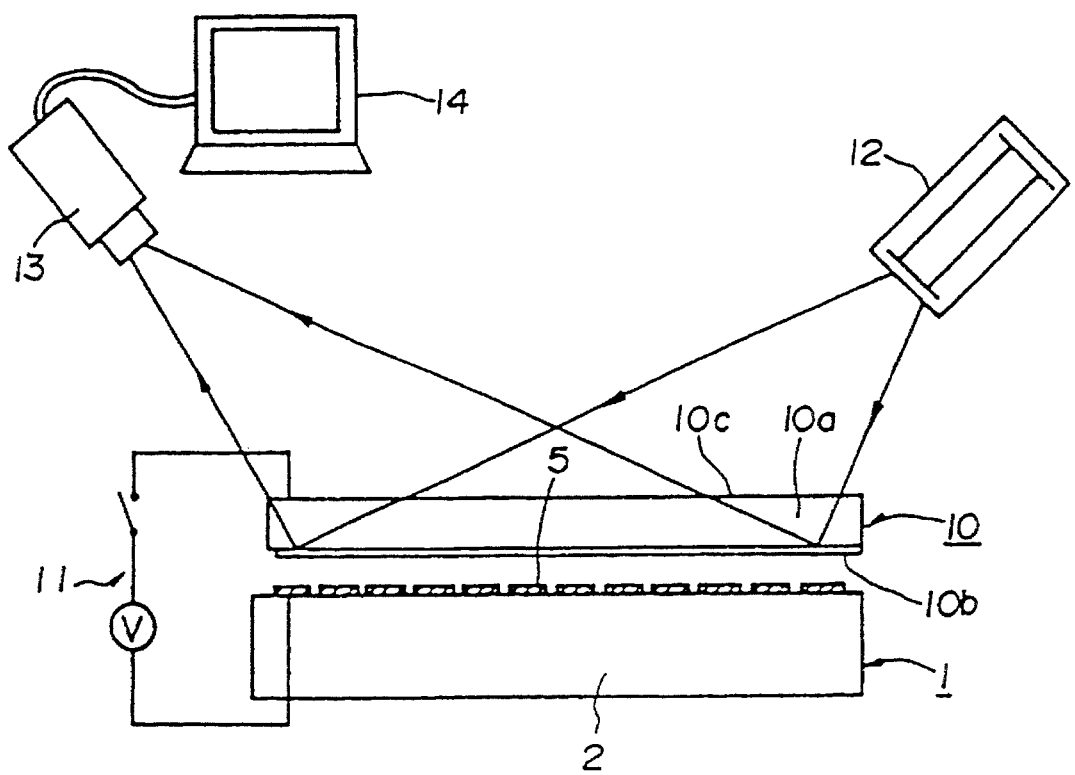
FIG. 6 is a drawing showing the basic structure of the test apparatus of the present invention.

The test equipment of the present invention detects flaws in Liquid Crystal Base Plate 1, primarily breaks and short circuits of Source Wiring 3 and Gate Wiring 4. Referring now to FIG. 6, reference number 10 represents electro-optical elements arranged with a small spacing of several (10) micrometers between the electro-optical element and Liquid Crystal Base Plate 1. Reference number 11 represents the power source for impressing an electric voltage between Electro-optical Element 10 and Pixel Element Terminal 5 of Liquid Crystal Base Plate 1. Reference number 12 represents a light source which irradiates the back (top side in FIG. 6) of Electro-optical Element 10. Reference number 13 represents the detection device for receiving the light reflected from Electro-optical Element 10. Reference number 14 represents a monitor for observing the pixel photographed by light detector 13.

Electro-optical Element 10 is a liquid crystal sheet or Pockell's crystal plate which changes optical characteristics when the electric field is impressed across it. The electro-optical element shown in FIG. 6 has a vapor coating, gold plated Light Reflector 10b formed on, or coating the bottom of Liquid Crystal Sheet 10a, and is enclosed within a transparent case. Thin Film Transparent Terminal 10c is formed at the top of Liquid Crystal Sheet 10a. Liquid Crystal Sheet 10a changes its optical transmissivity in proportion to the magnitude of the electric field across it. Liquid Crystal Sheet 10a is comprised of NCAP (Nematic Curvilinear Aligned Phase) material, or the like. Liquid crystal is enclosed within Liquid Crystal Sheet 10, and by adjusting the ratio of water drop shaped liquid crystal to that of a high density molecule, such as a polymer, the liquid crystal will exhibit transparent or opaque characteristics based on the aligning of the refractive index of the high density molecule and liquid crystal in response to the magnitude of the electric field applied across the liquid crystal. Another example of Electro-optical Element 10 uses Pockell's crystals which change the polarized light intensity of the reflected light in proportion to the size of the electric field across it. Other electro-optical elements can be used if the optical characteristics, such as optical transmissivity or refractive index of the reflected light, change at a constant rate when impressed with an electric field.

Power Source 11 is electrically connected to Thin Film Transparent Terminal 10c of Electro-optical Element 10 and Shorting-Bars 7 and 8 of Liquid Crystal Base Plate 1. A voltage can be applied through Source Wiring 3 and Gate Wiring 4 to all Pixel Elements 5 on Liquid Crystal Base Plate 1. A Power Source 11, which can impress a voltage pulse separately on Source Wiring 3 or Gate Wiring 4, and can change the pulse voltage level, pulse width, and repetition rate is preferred. Light Source 12 is a halogen lamp, however various laser beams or other uniform light sources can also be used. Light Detector 13 is a CCD camera, or the like.

Figure 2:
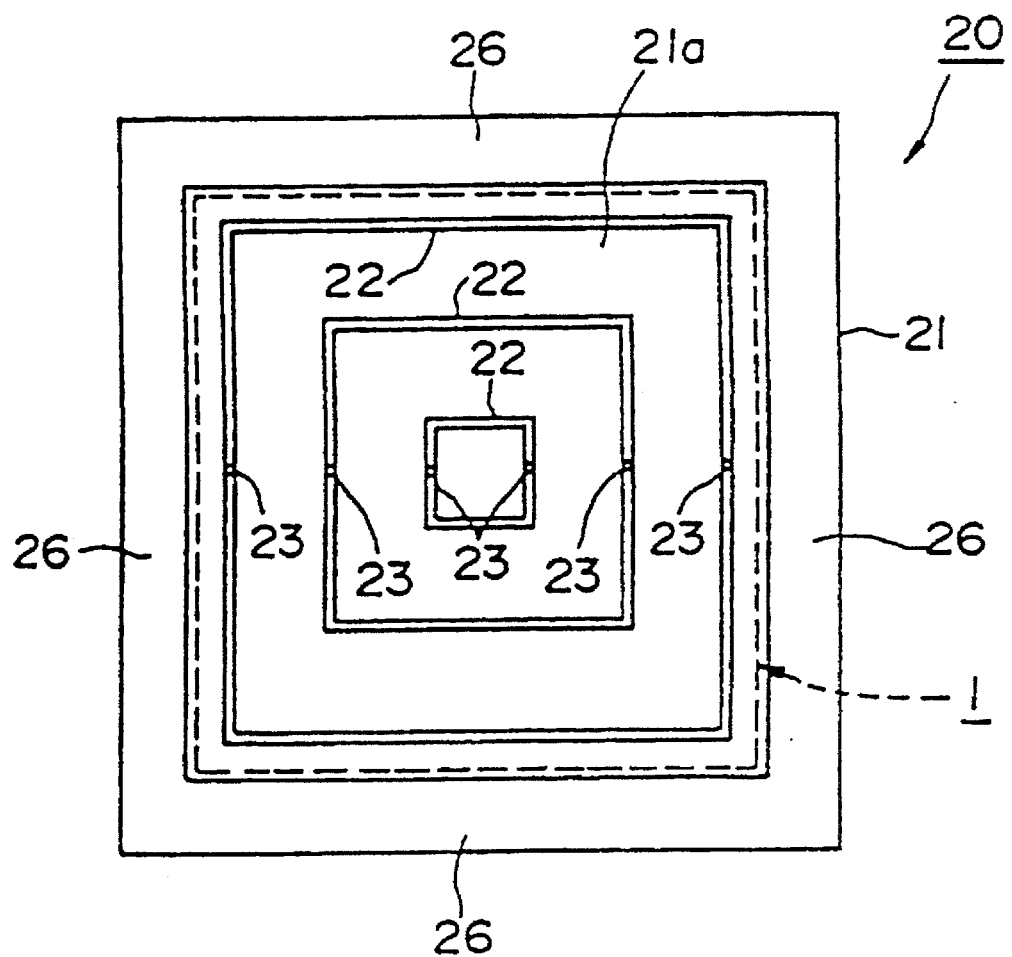
FIG. 2 is a diagram of the base platform of the same mounting device.

The material used to form Base Platform 21 is not critical, but it must have sufficient strength and be rust-proof, so stainless steel is used in the preferred embodiment. It is preferred that Base Platform 21 have a degree of flatness of about 0.1 um. To ensure such a degree of flatness it is recommended to subject Surface 21a to the Rapping process. Reference number 26 in FIGS. 1 and 2 is a guide piece formed on the outside of Base Platform 21 to position Liquid Crystal Base Plate 1. The test equipment will be used in a clean room, but it will be necessary to install the Vacuum Pump 25 outside of the clean room in order to maintain the integrity of the clean room.

Electro-optical Element 10 is attached to the bottom of Holder 30 by arranging Holder 30 on the top of Base Platform 21. After setting Liquid Crystal Base Plate 1 on Base Platform 21, Liquid Crystal Base Plate 1 and Electro-optical Element 10 are arranged to face each other. By measuring the gap between Liquid Crystal Base Plate 1 and Electro-optical Element 10 with a gap sensor while adjusting Setting Bolt 32 (which is attached to the outside of Bolt 30), the gap is set at the preferred value (about 30 um).

By adopting Mounting Device 20 in this manner, Liquid Crystal Base Plate 1 can be fixed easily and reliably to Base Platform 21 by vacuum attachment. Surface 21a of Base Platform 21 is flattened to a high degree of flatness such that even if warping or sinuosity has occurred in Liquid Crystal Base Plate 1, the warping or sinuosity will be eliminated by vacuum attachment in Base Platform 21. It is therefore possible to make the degree of flatness of Liquid Crystal Base Plate 1 approximately equal to that of Base Platform 21 at the time of testing, thereby enhancing test accuracy.

Figure 3:
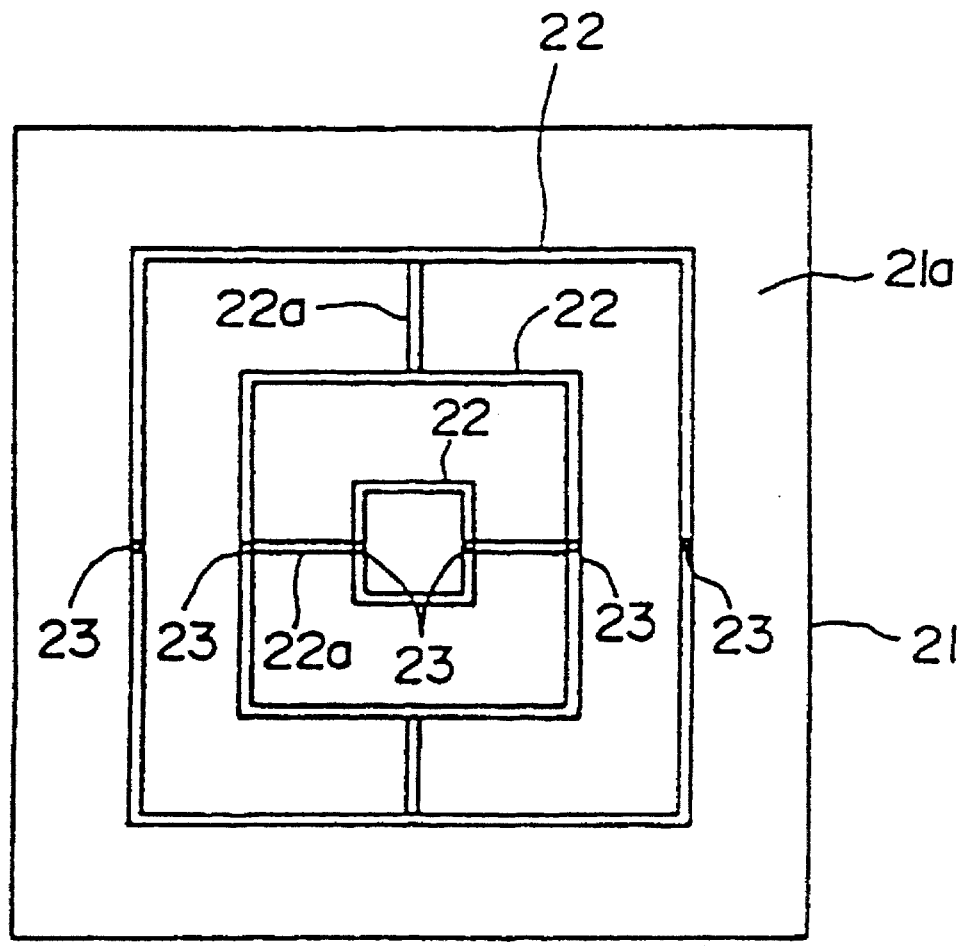
FIG. 3 is a diagram showing another example of the base platform.
Figure 4:
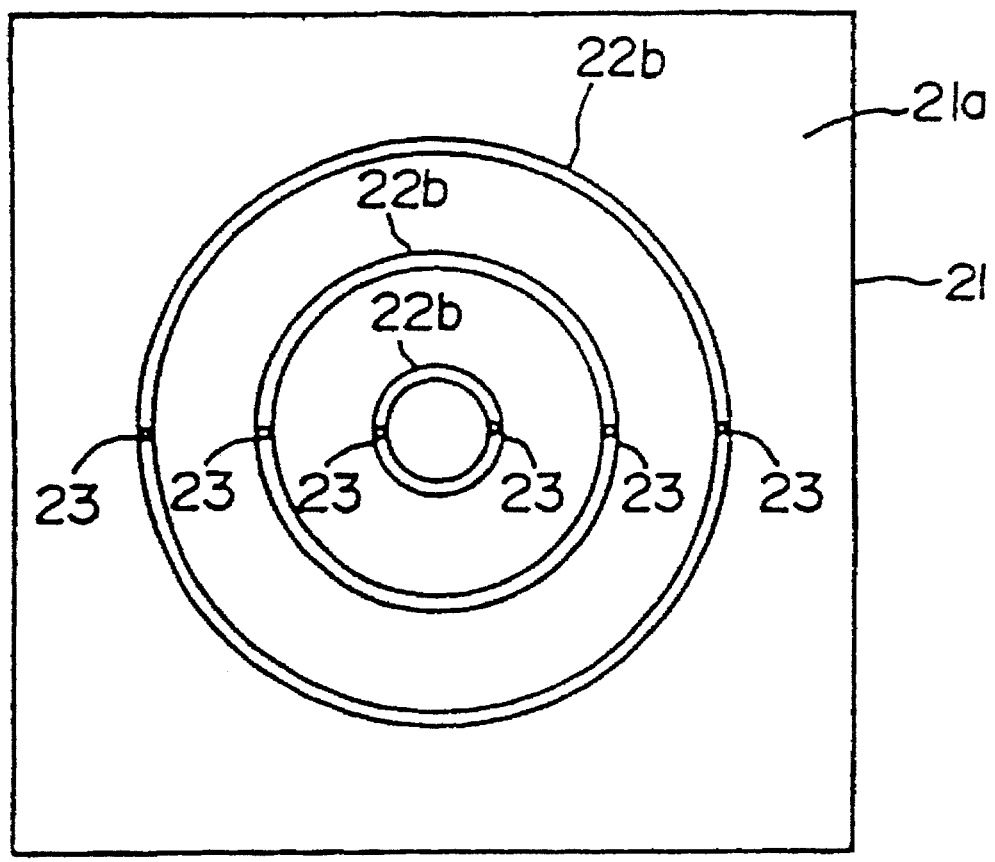
FIG. 4 is a diagram showing another example of the base platform.
Figure 5:
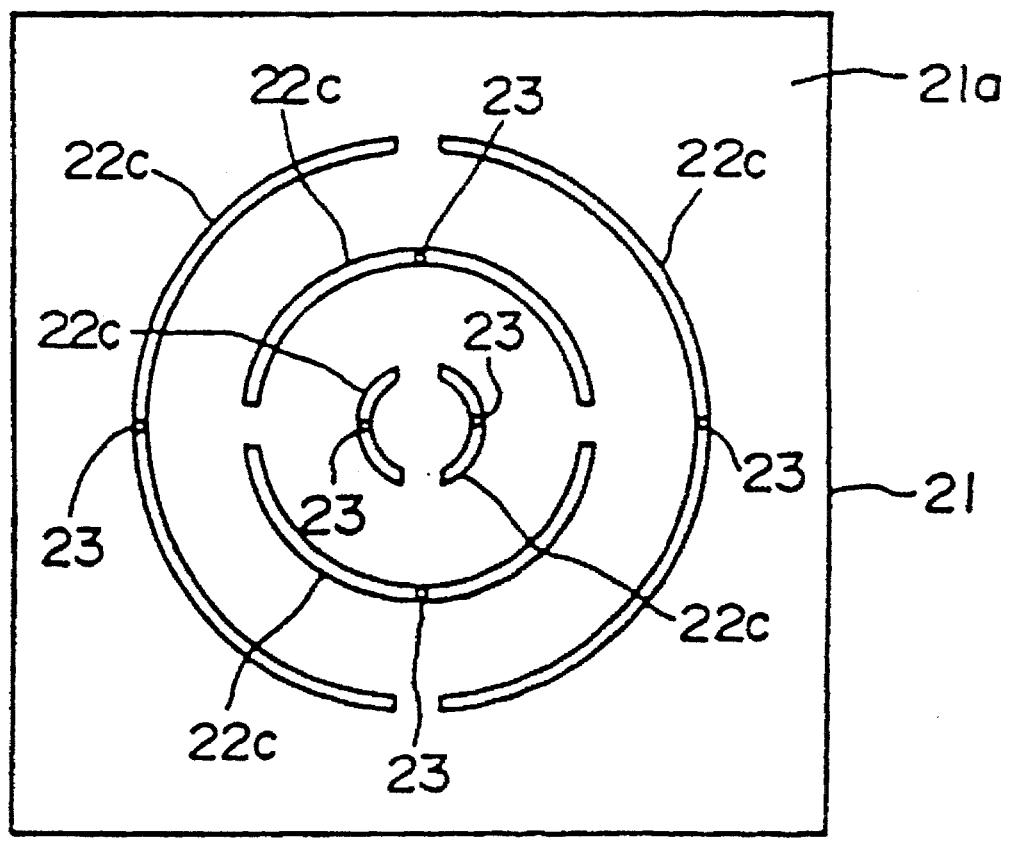
FIG. 5 is a diagram showing another example of the base platform.

The number and shape of Grooves 22 formed on Surface 21a of Base Platform 21 can be changed to correspond to the size and shape of the object of testing (Liquid Crystal Base Plate 1). As shown in FIG. 3, another Groove 22a can be formed to connect Groove 22 formed on Base Platform 21. As shown in FIG. 4, round Groove 22b can be formed in a concentric circle. As shown in FIG. 5, semi-circular arc Groove 22c can also be utilized. Other shapes such as rectangular, triangular, semi-circular, etc., can be adopted as the sectional shape of the groove, and the section size can also be discretionally fixed.

The testing device of the present invention can be applied not only to the liquid crystal display base plate of the Active Matrix Method, but similarly to any device that can be tested using this Simple Matrix Method.

The testing device of the present invention utilizes an electro-optical element that changes its optical characteristics when an electric field is applied across it and is constructed so that the light reflected from the electro-optical element is measured. Therefore, it is possible to test for flaws in the liquid crystal base plate itself during the manufacturing process, and thereby increase the yield and lower the cost of manufacturing liquid crystal base plates. A mounting device vacuum attaches the liquid crystal base plate to the base platform by applying a vacuum to the inside of a groove formed on the base platform surface. It is then possible to easily and reliably fix the liquid crystal base plate to the base platform at the time of testing and also to eliminate warping and sinuosity by sufficiently flattening the surface of the base platform. Consequently, accurate testing is accomplished.

What is claimed is:

1. A device for testing defects in a liquid crystal display base plate comprising:

a liquid crystal display base plate testing device placed facing the surface side of a liquid crystal display base plate;

an electro-optical element which changes its optical characteristics when an electric field from said liquid crystal display base plate is applied across it;

a power source to apply an electric voltage between said electro-optical element and each pixel element terminal of said liquid crystal display base plate;

irradiating light from a light source against the back side of said electro-optical element;

observing the reflected light received with a light detector;

a mounting device for fixing said liquid crystal display base plate during testing;

said mounting device having a flat surface and a base platform arranged so that the liquid crystal display base plate adheres to the surface of the mounting device;

a groove formed on the surface of the base platform; and a device for vacuum attachment of the liquid crystal display base plate to the surface of the base platform by applying a vacuum to said groove.

2. An apparatus for testing defects in liquid crystal display baseplates comprising:

a liquid crystal display baseplate to be tested;

an electro-optical element;

a voltage source;

a light source;

a mounting device; and a light detector;

said electro-optical element comprising a first and second side, said first side of said electro-optical element being coated with a transparent electrical conductor, said second side of said electro-optical element being coated with a non-conductive, optically reflective coating;

said liquid crystal display baseplate having a circuit side, and a second side;

said electro-optical element being placed adjacent to said liquid crystal display baseplate to be tested such that said second side of said electro-optical element is facing, and slightly spaced apart from said circuit side of said liquid crystal display baseplate;

said light source illuminating said first side of said said electro-optical element;

said voltage source electrically connected to said electrically conductive layer on said first side of said electro-optical element, and said circuitry on said liquid crystal display baseplate to be tested;

said voltage source applying a voltage between said electro-optical element, and said liquid crystal display baseplate such that an electric field is generated across said electro-optical element; and said light detector oriented such that it detects light reflected from said second side of said electro-optical element, such that defective circuitry on said circuit side of said liquid crystal display baseplate being testing will cause a variation in the electric field generated, and thus a variation in the light reflected by the electro-optical element.

3. The apparatus for testing defects in liquid crystal display baseplates as described in claim 2 which further includes a base platform; and a groove formed on the surface of said base platform, and a vacuum applied to said groove such that said liquid crystal display baseplate being tested is firmly attached to said base platform by application of said vacuum.

4. The apparatus for testing defects in liquid crystal display baseplates as described in claim 3 in which said base platform is formed of stainless steel.

5. The apparatus for testing defects in liquid crystal display baseplates as described in claim 3 in which said grooves are oriented such that by application of a vacuum of sufficient strength, said liquid crystal display base plate being tested can be held essentially flat against said base platform, temporarily curing any warping or sinuosity which may be present in said liquid crystal display base plate being tested.

6. The apparatus for testing defects in liquid crystal display baseplates as described in claim 2 in which said light source is located at an angle substantially perpendicular to said second surface of said electro-optical element.

7. The apparatus for testing defects in liquid crystal display baseplates as described in claim 2 in which said light detector is oriented at an angle substantially perpendicular to said second side of said electro-optical element.

8. The apparatus for testing defects in liquid crystal display baseplates as described in claim 2 in which said light source is a Tungsten lamp.

9. The device of claim 1 wherein said electro-optical element includes a first and a second side, said first side of said electro-optical element being coated with a transparent electrical conductor.

10. The device of claim 1 wherein said electro-optical element includes a first and a second side, said second side of said electro-optical element being coated with a non-conductive, optically reflective coating.

11. The device of claim 1 wherein said electro-optical element comprises NCAP material.

12. The device of claim 1 wherein said electro-optical element comprises Pockell's crystals.

13. The device of claim 1 wherein said base platform is rust-proof.

14. The device of claim 1 wherein said base platform includes a degree of flatness of about 0.1 microns.

15. The device of claim 1 wherein said base platform comprises stainless steel.

16. The device of claim 1 in which said groves are oriented such that by application of a vacuum of sufficient strength, said liquid crystal display base plate being tested can be held essentially flat against said base platform, temporarily curing any warping or sinuosity which may be present in said liquid crystal display base plate being tested.

17. The device of claim 9 in which said light source is located at an angle substantially perpendicular to said second side of said electro-optical element.

18. The device of claim 9 wherein said light detector is oriented at an angle substantially perpendicular to said second side of said electro-optical element.

19. The device of claim 1 wherein said light source is a tungsten lamp.

* * * * *